(12) United States Patent
Ambati

(10) Patent No.: US 8,008,092 B2
(45) Date of Patent: Aug. 30, 2011

(54) CCR3 INHIBITION FOR OCULAR ANGIOGENESIS AND MACULAR DEGENERATION

(75) Inventor: Jayakrishna Ambati, Lexington, KY (US)

(73) Assignee: University of Kentucky Research Foundation, Lexington, KY (US)

(*) Notice: Subject to any disclaimer, the term of this patent is extended or adjusted under 35 U.S.C. 154(b) by 0 days.

(21) Appl. No.: 12/247,722

(22) Filed: Oct. 8, 2008

(65) Prior Publication Data

US 2009/0123375 A1    May 14, 2009

Related U.S. Application Data

(60) Provisional application No. 60/998,348, filed on Oct. 9, 2007.

(51) Int. Cl.
*G01N 33/566* (2006.01)
*A61K 39/00* (2006.01)

(52) U.S. Cl. ............................... 436/501; 424/139.1
(58) Field of Classification Search .................. None
See application file for complete search history.

(56) References Cited

U.S. PATENT DOCUMENTS

| | | | |
|---|---|---|---|
| 6,207,155 B1 * | 3/2001 | Grimaldi et al. | 424/143.1 |
| 6,806,061 B1 * | 10/2004 | Gerard et al. | 435/69.1 |
| 2002/0147312 A1 * | 10/2002 | O'Keefe et al. | 530/387.3 |
| 2005/0069955 A1 * | 3/2005 | Plaksin et al. | 435/7.1 |
| 2005/0191702 A1 * | 9/2005 | Mack et al. | 435/7.1 |

* cited by examiner

*Primary Examiner* — Janet L Epps-Smith
(74) *Attorney, Agent, or Firm* — Crowell & Moring LLP (57) ABSTRACT

Provided are methods and compositions for the treatment or prevention of ocular angiogenesis and neovascularization. Administration of inhibitors of the CCR3 receptor or its ligands eotaxin (CCL11), eotaxin-2 (CCL24) or eotaxin-3 (CCL26) inhibits ocular angiogenesis.

1 Claim, 11 Drawing Sheets
(3 of 11 Drawing Sheet(s) Filed in Color)

Baseline

Figure 10B

Eotaxin 1

Eotaxin 2

Figure 10C

Eotaxin 3

Figure 10D

# CCR3 INHIBITION FOR OCULAR ANGIOGENESIS AND MACULAR DEGENERATION

CROSS-REFERENCE TO RELATED APPLICATION

This application is a non-provisional of U.S. application Ser. No. 60/998,348, filed Oct. 9, 2007, the entire disclosures of which are expressly incorporated by reference herein.

FIELD OF THE INVENTION

The present invention relates to the suppression of ocular angiogenesis by inhibiting the CCR3 receptor.

DESCRIPTION OF THE RELATED ART

The macula is the part of the retina which is responsible for central vision. Age-related macular degeneration is a chronic eye disease that occurs when tissue in the macula deteriorates. Macular affects central vision, but not peripheral vision. Macular degeneration is the leading cause of severe vision loss in people age 60 and older.

There are two forms of age-related macular degeneration: dry and wet. Dry macular degeneration is the most common type of macular degeneration and occurs when cells of the macula slowly begin to break down. Yellow deposits called "drusen" form under the retina between the retinal pigmented epithelium (RPE) and Bruch's membrane, which supports the retina. The drusen deposits are debris associated with compromised cell metabolism in the RPE. Eventually there is a deterioration of the macular regions associated with the drusen deposits resulting in a loss of central vision.

Wet macular degeneration occurs when abnormal bold vessels grow behind the macula. These vessels are fragile and can leak fluid and blood, which result in scarring of the macula and raise the potential for rapid, severe damage. Bruch's membrane breaks down, usually near drusen deposits. This is where new blood vessel growth, or neovascularization, occurs. Central vision can become distorted or lost entirely in a shore period of time, sometimes within days. Wet macular degeneration is responsible for about 10 percent of the cases of age-related macular degeneration, but it accounts for about 90 percent of the cases of legal blindness.

SUMMARY OF THE INVENTION

In one aspect, the present invention relates to a method of inhibiting ocular angiogenesis. The method comprises exposing a retinal or choroidal cell to a CCR3-inhibitory effective amount of a compound which inhibits the activity of CCR3. The present invention also relates to a composition for the inhibition of ocular angiogenesis. The composition comprises a compound which inhibits the activity of CCR3.

In another aspect, the present invention relates to a method of diagnosing or monitoring choroidal neovascularization or wet macular degeneration. The method comprises administering a labeled CCR3-specific binding molecule to a patient and detecting the presence or absence of the labeled molecule in the retina or choroid of the patient, the presence of the labeled molecule being indicative of choroidal neovascularization or wet macular degeneration. In still another aspect, the present invention relates to a method of treating choroidal neovascularization or wet macular degeneration. The method comprises administering an effective amount of a CCR3-specific binding molecule to a patient having, or at risk for having, choroidal neovascularization or wet macular degeneration.

The invention also relates to a method for screening for a compound that interacts with CCR3. In one aspect, the method comprises contacting CCR3 polypeptide or binding fragment thereof with a test compound, and determining if a complex is formed between CCR3 polypeptide or binding fragment thereof and the test compound. In another aspect, the test compound identified as interacting with CCR3 is assayed for the ability to inhibit ocular angiogenesis.

Other systems, methods, features and advantages of the present invention will be or become apparent to one with skill in the art upon examination of the following drawings and detailed description. It is intended that all such additional systems, methods, features and advantages be included within this description, be within the scope of the present invention, and be protected by the accompanying claims.

BRIEF DESCRIPTION OF THE DRAWINGS

The file of this patent contains at least one drawing executed in color. Copies of this patent with color drawings (s) will be provided by the Patent and Trademark Office upon request and payment of the necessary fee.

FIG. 10A presents fluorescent microscopic images seen from the fluorescent baseplate assay. FIG. 10A shows the untreated baseline cultures. Minimal fluorescence was seen in the untreated baseline cultures which were approximately 70-80% confluent. FIG. 10D shows assay results with eotaxin 3. After 10 seconds of eotaxin stimulation, hCEC cultures exhibited increased fluorescence and cord formation characteristic of F-actin polymerization. Scale bars 50 µm.

FIG. 11 presents a Rac-1 activation assay.

DETAILED DESCRIPTION

Intraocular inflammation is not clinically apparent in age-related macular degeneration. However, there is evidence suggesting an influential role for inflammation in this condition. CCR3 is a promiscuous chemokine receptor that is predominantly expressed by eosinophils but also is found on other leukocytes and some endothelial and epithelial cells.

The invention relates to methods and compositions for the treatment or prevention of ocular angiogenesis and neovascularization. Administration of inhibitors of the CCR3 receptor or its ligands, for example eotaxin (CCL11), eotaxin-2 (CCL24) or eotaxin-3 (CCL26), inhibits ocular angiogenesis. Ocular angiogenesis includes choroidal angiogenesis and retinal angiogenesis. Compositions and methods for inhibiting CCR3, eotaxin (CCL11), eotaxin-2 (CCL24), and eotaxin-3 (CCL26) for the treatment and/or prevention of neovascular disease are provided. Also provided are novel therapeutic targets and diagnostic markers for choroidal neovascularization.

Any compound which inhibits the activity of CCR3 may be used in the present invention. Such compounds include inhibitory molecules which bind directly to the CCR3 receptor, antibodies which bind the CCR3 receptor or to the natural ligands of the CCR3 receptor, including eotaxin (CCL11), eotaxin-2 (CCL24) and eotaxin-3 (CCL26), RNA, DNA or RNA/DNA aptamers which specifically bind CCR3, eotaxin, eotaxin-2 or eotaxin-3, and siRNA or anti-sense oligonucleotides which inhibit the expression of CCR3, eotaxin, eotaxin-2 or eotaxin-3. Additional compounds which inhibit the activity of CCR3 include inhibitory molecules which specifically bind CCR3, eotaxin, eotaxin-2 or eotaxin-3, including an oligopeptide, small molecule antagonist (e.g., organic molecule having a molecular weight less than 2000, or less than 1000, or less than 500), ribozyme, intrabody or intraceptor. An intrabody refers to an antibody produced intracellularly, for example, a single chain antibody (such as a single chain Fv antibody fragment) expressed inside a cell transformed with an appropriate exogenous nucleic acid. An intraceptor refers to an receptor (such as a receptor for CCR3, eotaxin, eotaxin-2 or eotaxin-3) produced intracellularly, for example, a CCR3, eotaxin, eotaxin-2 or eotaxin-3 receptor expressed inside a cell transformed with an appropriate exogenous nucleic acid.

Numerous "small molecule" inhibitors for the CCR3 receptor have been developed and can be used in the present invention. In one aspect the CCR3 inhibitor is an organic molecule having a molecular weight less than 2000. In another aspect of the invention, the CCR3 inhibitor is an organic molecule having a molecular weight less than 1000. In yet another aspect of the invention, the CCR3 inhibitor is an organic molecule having a molecular weight less than 500. The CCR3 receptor inhibitors include piperidine derivatives, piperidine amides and biperidine compounds such as those described in U.S. Pat. Nos. 6,984,651 and 6,903,115, and U.S. published applications 20050176708, 20050182094 and 20050182095; heterocyclic piperidines such as those described in U.S. Pat. No. 6,759,411; diphenyl-piperidine derivatives such as those described in U.S. Pat. No. 6,566,376; 2,5-substituted pyrimidine derivatives such as those described in U.S. Pat. No. 6,984,643; piperizinones such as those described in U.S. Pat. No. 6,974,869; bicycylic and tricyclic amines such as those described in U.S. Pat. No. 6,960,666; N-ureidoalkyl-piperidines such as those described in U.S. Pat. Nos. 6,949,546, 6,919,368, 6,906,066, 6,897,234, 6,875,776, 6,780,857, 6,627,629, 6,521,592 and 6,331,541; bicyclic diamines such as those described in U.S. Pat. No. 6,821,964; benzylcycloalkyl amines such as those described in U.S. Pat. No. 6,864,380; 2-substituted-4-nitrogen heterocycles such as those described in U.S. Pat. No. 6,706,735; ureido derivatives of poly-4-amino-2-carboxy-1-methyl pyrrole compounds; bicyclic and bridged nitrogen heterocycles such as those described in U.S. published application 20050234034; azetidine derivatives such as those described in U.S. published application 20050222118; substituted fused bicyclic amines such as those described in U.S. published application 20050197373; substituted spiro azabicyclics such as those described in U.S. published application 20050197325; piperidine-substituted indoles or heteroderivatives thereof such as those described in U.S. published application 20050153979; piperidinyl and piperazinyl compounds substituted with bicyclo-heterocyclylalkyl groups such as those described in U.S. published application 20050090504; arylsulfonamide derivatives such as those described in U.S. published application 20050070582; 1-phenyl-1,2-diaminoethane derivatives such as those described in U.S. published application 20040063779; (N-{[2S]-4-(3,4-dichlorobenzyl)morpholin-2-yl}methyl)-N'[(2-methyl-2H-tetraazol-5-yl)methyl]urea) (see, e.g., Nakamura et al., Immunol Res., 33:213-222, 2006; N-{(3R)-1-[(6-fluoro-2-naphthyl)methyl]pyrrolidin-3-yl}-2-{1-[(3-methyl-1-oxidopyridin-2-yl)carbonyl]piperidin-4-ylidene}acetamide (see, e.g., Suzuki et al., Biochem. Biophys. Res. Commun., 339:1217-1223, 2006; N-{(3R)-1-[(6-fluoro-2-naphthyl)methyl]pyrrolidin-3-yl}-2-{1-[(5-hydroxy-3-methylpyridin-2-yl)carbonyl]piperidin-4-ylidene}acetamide hemifumarate (see, e.g., Morokata et al., J. Pharmacol. Exp. Ther., Dec. 9, 2005 [Epub ahead of print]); bipiperidine amide antagonists of CCR3 such as those described in Ting et al., Bioorg. Med. Chem. Lett., 15:3020-3023, 2005; (S)-methyl-2-naphthoylamino-3-(4-nitrophenyl)propionate (see, e.g., Beasley et al., J. Allergy Clin. Immunol., 105: S466-S472, 2000; and the CCR3 antagonist compounds described in Fryer et al., J. Clin. Invest., 116:228-236, 2006.

Additional compounds for inhibiting the CCR3 receptor include RNA, DNA or RNA/DNA aptamers directed against CCR3, eotaxin, eotaxin-2 or eotaxin-3. Exemplary methods for making aptamers are described in U.S. Pat. Nos. 5,270,163, 5,840,867, 6,180,348 and 6,699,843.

Additional compounds for inhibiting the CCR3 receptor include anti-sense oligonucleotides or siRNAs directed against CCR3, eotaxin, eotaxin-2 or eotaxin-3, including the anti-sense oligonucleotides directed against the CCR3 receptor such as that described in U.S. Pat. No. 6,822,087.

The siRNAs for use in the present invention are designed according to standard methods in the field of RNA interference. Introduction of siRNAs into cells may be by transfection with expression vectors, by transfection with synthetic dsRNA, or by any other appropriate method. Transfection with expression vectors is preferred.

The expression vectors which can be used to deliver siRNA according to the invention include retroviral, adenoviral and lentiviral vectors. The expression vector includes a sequence which codes for a portion of the target gene (e.g., CCR3 receptor, eotaxin, eotaxin-2 or eotaxin-3) which is to be silenced. The target gene sequence is designed such that, upon transcription in the transfected host, the target RNA sequence forms a hairpin structure due to the presence of self-complementary bases. Processing within the cell removes the loop resulting in formation of a siRNA duplex. The double stranded RNA sequence should be less than 30 nucleotide bases; preferably the dsRNA sequence is 19-25 bases in length; more preferably the dsRNA sequence is 20 nucleotides in length.

The expression vectors may include one or more promoter regions to enhance synthesis of the target gene sequence. Promoters which can be used include CMV promoter, SV40 promoter, promoter of mouse U6 gene, and promoter of human H1 gene.

One or more selection markers may be included to facilitate transfection with the expression vector. The selection marker may be included within the expression vector, or may be introduced on a separate genetic element. For example, the bacterial hygromycin B phosphotransferase gene may be used as a selection marker, with cells being grown in the presence of hygromycin to select for those cells transfected with the aforementioned gene.

Synthetic dsRNA may also be introduced into cells to provide gene silencing by siRNA. The synthetic dsRNAs are less than 30 base pairs in length. Preferably the synthetic dsRNAs are 19-25 base pairs in length. More preferably the dsRNAs are 19, 20 or 21 base pairs in length, optionally with 2-nucleotide 3' overhangs. The 3' overhangs are preferably TT residues.

Synthetic dsRNAs can be introduced into cells by injection, by complexing with agents such as cationic lipids, by use of a gene gun, or by any other appropriate method.

Additional compounds for inhibiting the CCR3 receptor include antibodies which specifically bind the CCR3 receptor, eotaxin, eotaxin-2 or eotaxin-3. Exemplary antibodies which specifically bind and inhibit the CCR3 receptor are described in U.S. Pat. Nos. 6,806,061 and 6,207,155, and in U.S. published applications 20050191702, 20050069955, and 20020147312. Exemplary antibodies which specifically bind and inhibit eotaxin and eotaxin-2 are described in U.S. Pat. Nos. 6,946,546 and 6,635,251, and in U.S. published applications 20040191255 and 20040014132.

The antibodies of the present invention can be polyclonal or monoclonal, and the term antibody is intended to encompass both polyclonal and monoclonal antibodies. Antibodies of the present invention can be raised against an appropriate immunogen, including proteins or polypeptides of the present invention, such as isolated and/or recombinant mammalian CCR3 receptor, eotaxin, eotaxin-2 or eotaxin-3 protein or portion thereof, or synthetic molecules, such as synthetic peptides.

Preparation of immunizing antigen, and polyclonal and monoclonal antibody production can be performed using any suitable technique. A variety of methods have been described (see e.g., Kohler et al., Nature, 256: 495-497 (1975) and Eur. J. Immunol. 6: 511-519 (1976); Milstein et al., Nature 266: 550-552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 27, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0) with antibody producing cells. The antibody producing cell, preferably those of the spleen or lymph nodes, are obtained from animals immunized with the antigen of interest. The fused cells (hybridomas) are isolated using selective culture conditions, and cloned by limiting dilution. Cells which produce antibodies with the desired specificity are selected by a suitable assay (e.g., ELISA).

Single chain antibodies, and chimeric, humanized or primatized (CDR-grafted) antibodies, as well as chimeric or CDR-grafted single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023. B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single chain antibodies.

In addition, functional fragments of antibodies, including fragments of chimeric, humanized, primatized or single chain antibodies, can also be produced. Functional fragments of foregoing antibodies retain at least one binding function and/or modulation function of the full-length antibody from which they are derived. For example, antibody fragments capable of binding to a mammalian CCR3 receptor, eotaxin, eotaxin-2 or eotaxin-3 or portion thereof, including, but not limited to, Fv, Fab, Fab' and F(ab').sub.2 fragments are encompassed by the invention. Such fragments can be produced by enzymatic cleavage or by recombinant techniques. For instance, papain or pepsin cleavage can generate Fab or F(ab').sub.2 fragments, respectively. Alternatively, antibodies can be produced in a variety of truncated forms using antibody genes in which one or more stop codons has been introduced upstream of the natural stop site. For example, a chimeric gene encoding a F(ab').sub.2 heavy chain portion can be designed to include DNA sequences encoding the CH.sub.1 domain and hinge region of the heavy chain.

The antibodies of the present invention can be used to modulate receptor or ligand function in research and therapeutic applications. For instance, antibodies can act as inhibitors to inhibit (reduce or prevent) (a) binding (e.g., of a ligand, a second inhibitor or a promoter) to the receptor, (b) a receptor signalling, (c) and/or a stimulatory function. Antibodies which act as inhibitors of receptor function can block ligand or promoter binding directly or indirectly (e.g., by causing a conformational change). For example, antibodies can inhibit receptor function by inhibiting binding of a ligand, or by desensitization (with or without inhibition of binding of a ligand).

Anti-idiotypic antibodies. are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See e.g., U.S. Pat. No. 4,699,880. Single chain, and chimeric, humanized or primatized (CDR-grafted), as well as chimeric or CDR-grafted single chain anti-idiotypic antibodies can be prepared, and are encompassed by the term anti-idiotypic antibody. Antibody fragments of such antibodies can also be prepared.

Modulation of mammalian CCR3 receptor function according to the present invention, through the inhibition of at least one function characteristic of a mammalian CCR3 receptor, provides an effective and selective way of inhibiting ocular angiogenesis. One or more inhibitors of CCR3 receptor function, such as those identified as described herein, can be used to inhibit ocular angiogenesis for therapeutic purposes.

Thus, the present invention provides a method of inhibiting ocular angiogenesis in an individual in need of such therapy, comprising administering a compound which inhibits mammalian CCR3 receptor function to an individual in need of such therapy. Such individuals include those having age-related macular degeneration.

The present inventors have found that CCR3 is highly expressed by endothelial cells of choroidal neovascularization membrane in patients with wet age-related macular degeneration. Thus, in one aspect of the invention, CCR3 expression is used as a target for diagnosis or therapy of choroidal neovascularization or wet age-related macular degeneration. For diagnosis of choroidal neovascularization or wet macular degeneration, a molecule which can specifically bind CCR3 or any portion thereof (e.g., an antibody) is administered to the patient. A reporter group is attached to the CCR3-specific binding molecule so that in situ expression of CCR3 can be monitored. Appropriate reporter groups include fluorescent dyes, radionuclides, and dense metal particles, although any appropriate detectable reporter group can be used. An abundance of CCR3-specific binding molecule detected in the retina or choroid would be indicative of choroidal neovascularization or wet macular degeneration. Early detection of CCR3 overexpression in the retina or choroid before overt signs of macular degeneration develop allows for therapy to be initiated early, even before choroidal neovascularization takes place, thereby leading to more effective treatment of the disease. In addition, administration of the labeled CCR3-specific binding molecule can be used to monitor the progress of any therapy.

Administration of CCR3-specific binding molecule can also be used as a way of treating choroidal neovascularization or wet macular degeneration. The CCR3-specific binding molecule can act directly by removing CCR3, thereby stopping or reducing neovascularization. In another aspect, the CCR3-specific binding molecule can have attached to it a toxin, radionuclide or other entity which kills or inhibits the cells involved in neovascularization. Alternatively, a CCR3-specific binding molecule can be administered to the patient in conjunction with, or followed by, administration of a second molecule which specifically binds the CCR3-specific binding molecule. A toxin, radionuclide or other entity which kills or inhibits the cells involved in neovascularization is attached to the second molecule, thereby providing for treatment of choroidal neovascularization or wet macular degeneration.

The methods of the present invention can be used in any mammalian species, including human, monkey, cow, sheep, pig, goat, horse, mouse, rat, dog, cat, rabbit, guinea pig, hamster and horse. Humans are preferred.

According to the method of the invention, one or more compounds can be administered to the host by an appropriate route, either alone or in combination with another drug. An effective amount of a compound (e.g., a small molecule CCR3 receptor antagonist which inhibits ligand binding, an antibody or an siRNA) is administered. An effective amount is an amount sufficient to achieve the desired therapeutic effect, under the conditions of administration, such as an amount sufficient for inhibition of a CCR3 receptor function, and thereby inhibition of ocular angiogenesis.

A variety of routes of administration are possible including, but not necessarily limited to oral, dietary, topical (e.g., eye drops), parenteral (e.g., intravenous, intraarterial, intramuscular, subcutaneous injection), inhalation (e.g., intrabronchial, intranasal or oral inhalation, intranasal drops), and intraocular injection routes of administration, depending on the disease or condition to be treated. Intraocular injection routes include periocular (subconjunctival/transscleral), intravitreous, subretinal, suprachoroidal and intracameral modes of injection.

Formulation of a compound to be administered will vary according to the route of administration selected (e.g., solution, emulsion, capsule). An appropriate composition comprising the compound to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers (See, generally, Remington's Pharmaceutical Science, 16th Edition, Mack, Ed. 1980). For inhalation, the compound is solubilized and loaded into a suitable dispenser for administration (e.g., an atomizer, nebulizer or pressurized aerosol dispenser). As another example, a compound may be administered via a sustained release device or composition which is implanted in the vitreous humor, aqueous humor, on the sclera, in the sclera, in the suprachoroidal space, or in the subretinal space.

In another embodiment, the present invention provides methods for screening compounds that interact with CCR3. The present invention is useful for screening compounds by using CCR3 polypeptide or binding fragments thereof in any of a variety of drug screening techniques. The CCR3 polypeptide or fragment employed in such a test may either be free in solution, affixed to a solid support, borne on a cell surface or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. Such cells, either in viable or fixed form, can be used for standard binding assays. One may measure, for example, the formation of complexes between CCR3 and the agent being tested. Alternatively, one can examine the diminution in complex formation between CCR3 and its target cell, monocyte, etc. caused by the agent being tested.

Thus, the present invention provides methods of screening for drugs or any other agents which can affect ocular angiogenesis and disease. These methods comprise contacting such an agent with a CCR3 polypeptide or fragment thereof and assaying (i) for the presence of a complex between the agent and the CCR3 polypeptide or fragment, or (ii) for the presence of a complex between the CCR3 polypeptide or fragment and the cell, by methods well known in the art. In such competitive binding assays, the CCR3 polypeptide or fragment is typically labeled. After suitable incubation, free CCR3 polypeptide or fragment is separated from that present in bound form, and the amount of free or uncomplexed label is a measure of the ability of the particular agent to bind to CCR3 or to interfere with the CCR3 and agent complex.

Another technique for drug screening provides high throughput screening for compounds having suitable binding affinity to the CCR3 polypeptide and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with CCR3 polypeptide and washed. Bound CCR3 polypeptide is then detected by methods well known in the art. Purified CCR3 can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding CCR3 specifically compete with a test compound for binding to CCR3 polypeptides or fragments thereof. In this manner, the antibodies can be used to detect the presence of any peptide which shares one or more antigenic determinants with CCR3.

The present invention also contemplates the use of drug screening assays in which drugs or any other agents are monitored in a bioassay, such as the ability of the drug or agent to inhibit ocular angiogenesis. Such a drug screening assay may be used in conjunction with the various binding assays described above, i.e., drugs or other agents may be first tested for their ability to bind to CCR3, and those compounds having binding affinity for CCR3 are then tested in a bioassay, such as the ability of the drug or agent to inhibit ocular angiogenesis. Alternatively, the bioassay may be conducted with the drug or agent with or without a compound which blocks the action of CCR3, such as an antibody against CCR3. Inhibition of ocular angiogenesis with the drug or agent but no inhibition of ocular angiogenesis with drug or agent in the presence of a compound which blocks the action of CCR3 would be indicative of a compound that inhibits ocular angiogenesis by interacting with CCR3. Similar screening assays can be performed comparing ocular angiogenesis in wild-type cells versus cells in which the genes for CCR3 are knocked out, with inhibition of ocular angiogenesis in wild-type cells due to exposure to drug agent and no inhibition in the knockout cells being indicative of the drug or agent inhibiting ocular angiogenesis by interacting with CCR3.

Example 1

Methods

Laser photocoagulation (532 nm, 200 mW, 100 ms, 75 μm) (OcuLight GL, Iridex Corporation) was performed (volume studies: 3/eye; protein analyses/flow cytometry: 12/eye) on both eyes of each animal to induce CNV (choroidal neovascularization). CNV volumes were measured by scanning laser confocal microscope (TCS SP, Leica) with 0.5% FITC-*Griffonia simplicifolia* Isolectin B4 (Vector Laboratories). CNV was induced by laser injury in C57BL/6J and Ccr3$^{-/-}$ mice and volumes measured 7 days later by confocal evaluation of *Griffonia simplicifolia* Isolectin B4 staining of RPE-choroid flatmounts. Neutralizing antibodies (Ab) against CCR3, eotaxin (CCL-11), eotaxin-2 (CCL-24), RANTES, MCP-3 or control goat IgG or rat IgG$_{2a}$ were injected into the vitreous humor following injury.

Flow cytometry was used to determine the numbers of eosinophils, mast cells and macrophages in the choroid, expression of CCR3 by various cell types in the eye, and the cell cycle state of choroidal endothelial cells (CECs) in vivo. Suspensions of cells isolated from mouse RPE/choroid by incubation with collagenase D (20 U/ml; Roche Diagnostics) treatment were incubated in Fc block (0.5 mg/ml; BD Pharmingen) for 15 min on ice. Rat antibody to mouse CCR3 (1:250; Santa Cruz) coupled with PE-donkey antibody to rat IgG (1:250; Jackson Immunoresearch) were used to quantify cell surface receptor expression on choroidal endothelial cells, defined by CD31$^+$VEGFR-2$^+$ expression, gated by FITC-conjugated rat antibody to mouse CD31 (1:250; BD Biosciences) and PerCP-Cy5.5-conjugated rat antibody to mouse CD11b (1:50; BD Biosciences). Macrophages, neutrophils, eosinophils and mast cells were defined as F4/80$^+$ CD11c$^-$, Gr-1$^+$F4/80$^-$, CCR3$^{hi}$CD3$^-$CD117$^{int}$CD49d$^+$ and CCR3$^{int}$CD3$^-$CD117$^{hi}$CD49d$^+$ cells, respectively. DNA content for cell cycle was analyzed after incubation with propidium iodide (0.05 mg/ml; Molecular Probes) containing 0.1% Triton X-100 and RNase A (0.1 mg/ml; Roche).

Because the probability of each laser lesion developing CNV is influenced by the group to which it belongs, the mouse, the eye, and the laser spot, the mean lesion volumes were compared using a linear mixed model with a split plot repeated measures design. The whole plot factor was the genetic group to which the animal belonged while the split plot factor was the eye. Statistical significance was determined at the 0.05 level. Post hoc comparison of means was constructed with a Bonferroni adjustment for multiple comparisons.

Results

Figure 1:
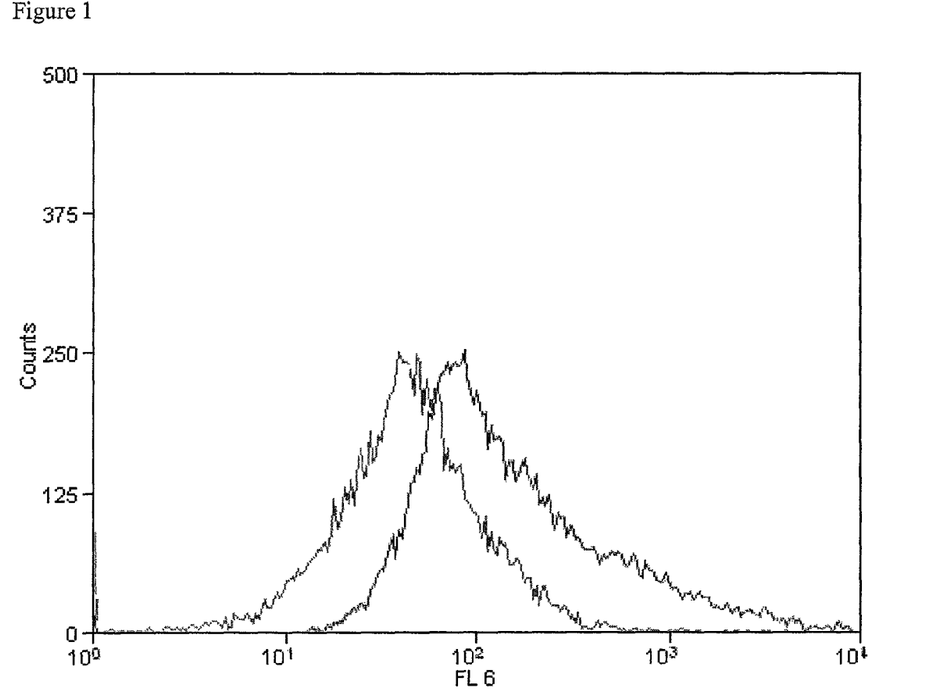
FIG. 1 illustrates the effect of laser injury on the number of CCR3 receptors on choroidal endothelial cells.
Figure 2:
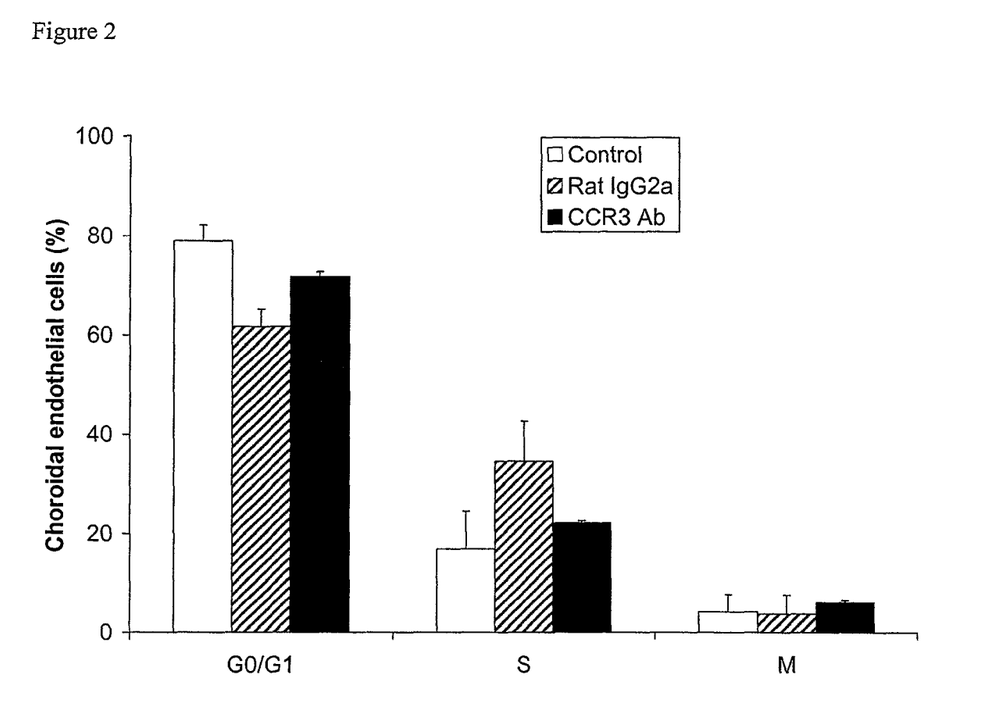
FIG. 2 shows the effect of CCR3 antibody on the proliferation of choroidal endothelial cells following laser injury.
Figure 3:
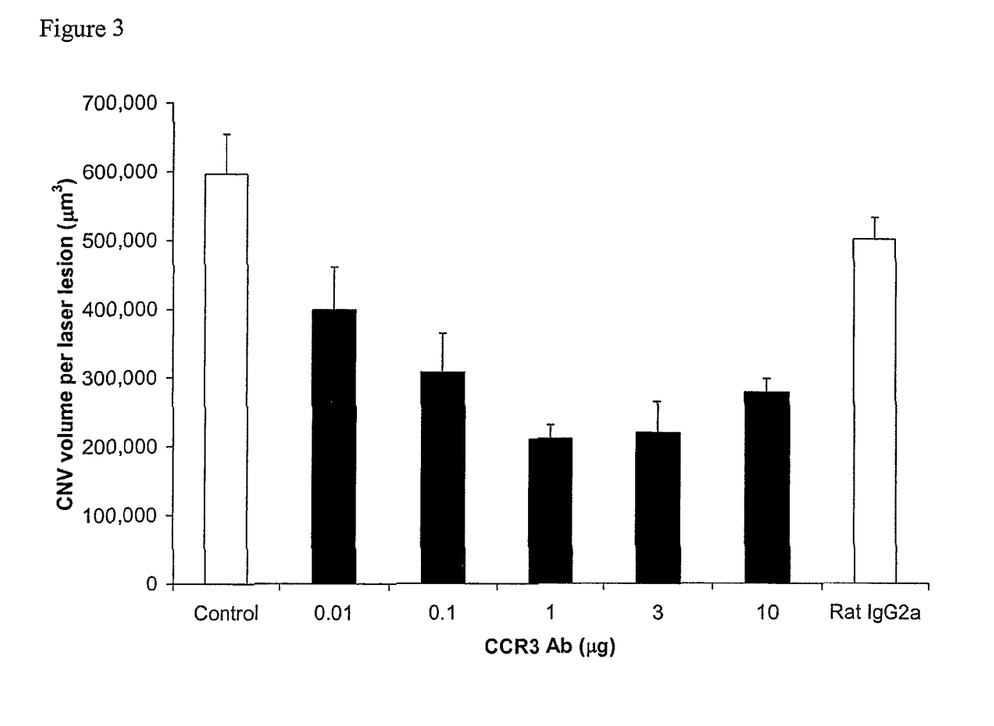
FIG. 3 illustrates the dose-dependent effect of CCR3 antibody on choroidal neovascularization volume
Figure 4:
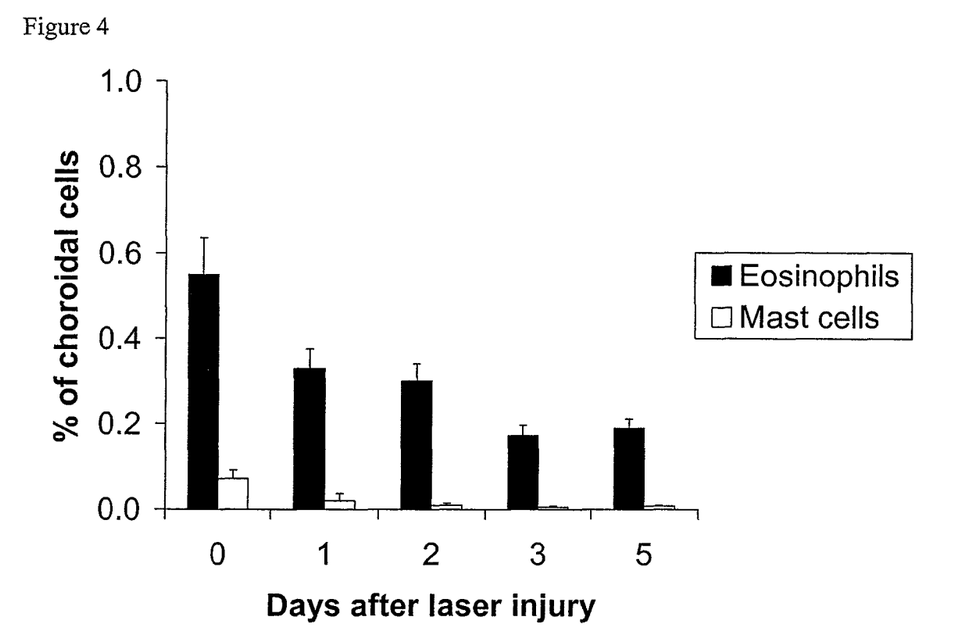
FIG. 4 shows lack of infiltration of eosinophils and mast cells into the choroid following laser injury.
Figure 5:
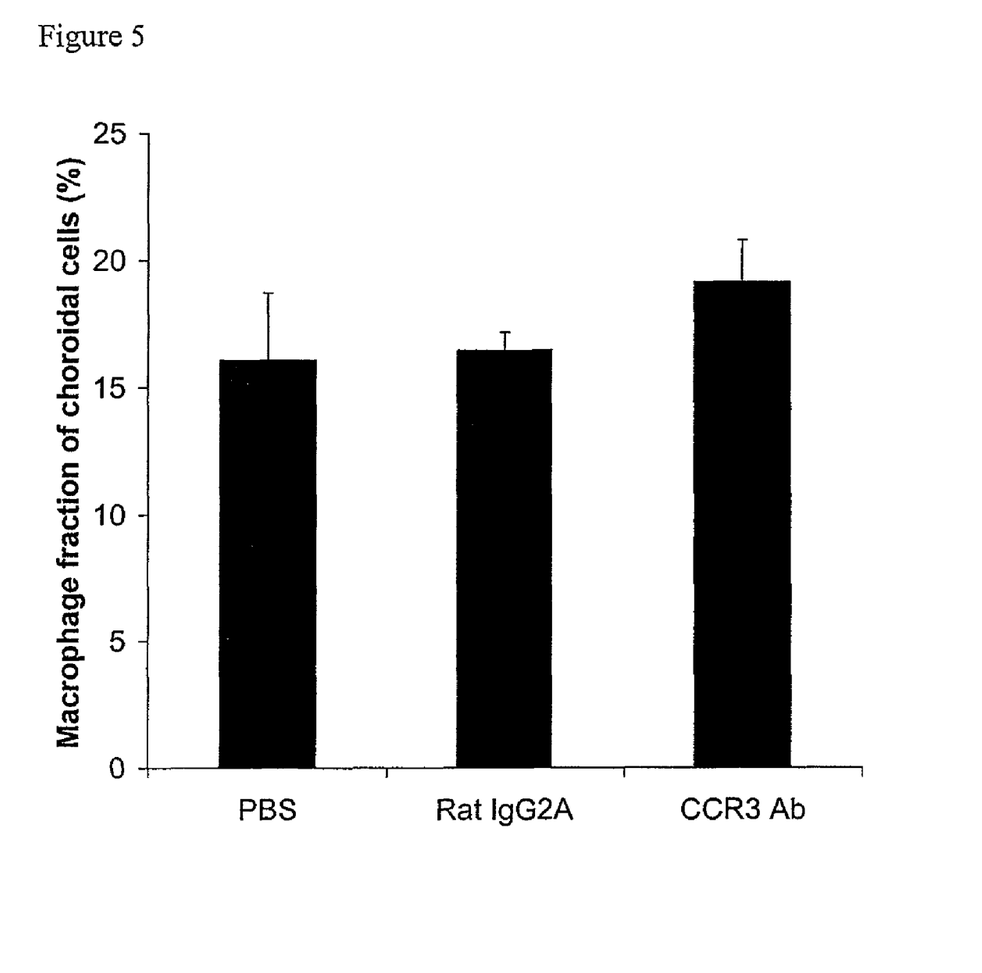
FIG. 5 illustrates the lack of change of number of infiltrating macrophages in the choroid following laser injury and CCR3 antibody treatment.

As illustrated by FIG. 1, the number of CCR3 receptors on choroidal endothelial cells in vivo following laser injury (red) is significantly greater than the number before injury (green), indicating upregulation of CCR3 receptors on these cells. Eosinophils or mast cells are the principal cells in most systems that respond to CCR3. However, the number of eosinophils and mast cells in the choroid was unaffected by injury or CCR3 Ab (FIG. 4). CCR3 Ab did not inhibit choroidal macrophage infiltration following injury (FIG. 5), indicating that laser injury is not working by anti-inflammatory means. As illustrated by FIG. 3, CCR3 Ab suppressed CNV volume in C57BL/6J mice by nearly 60% in a dose-dependent and statistically significant manner compared to vehicle control (PBS) and control antibody (rat IgG2a). FIG. 2 demonstrates that CCR3 Ab blockade, but not control antibody (rat IgG2a), inhibited proliferation (S phase) of CECs (choroidal endothelial cells) in vivo following laser injury. Experiments in Ccr3−/− mice confirmed these results. Of the CCR3 ligands, blockade of only eotaxin (45%) or eotaxin-2 (70%) suppressed CNV in C57BL/6J mice compared to control antibodies (all Ps<0.001). Experiments in Ccl11−/− and Ccl24−/− mice confirmed these results.

These findings demonstrate that CCR3 receptor promotes angiogenesis not via leukocyte modulation but rather by direct effects on CECs. Thus, CCL-11, CCL-24, and CCR3 are new targets for neovascular AMD (age-related macular degeneration).

Example 2

Methods

Male C57BL/6J mice (Jackson Laboratories) between 6 and 8 weeks of age were used to minimize variability. For all procedures, anesthesia was achieved by intraperitoneal injection of 50 mg/kg ketamine hydrochloride (Ft. Dodge Animal Health) and 10 mg/kg xylazine (Phoenix Scientific), and pupils were dilated with topical 1% tropicamide (Alcon Laboratories).

Laser photocoagulation (532 nm, 200 mW, 100 ms, 75 μm) (OcuLight GL, Iridex Corporation) was performed (volume studies: 3/eye; protein analyses/flow cytometry: 12/eye) on both eyes of each animal to induce CNV. CNV volumes were measured by scanning laser confocal microscope (TCS SP, Leica) with 0.5% FITC-Griffonia simplicifolia Isolectin B4 (Vector Laboratories) or 0.5% FITC-rat antibody against mouse CD31 (BD Biosciences). Volumes obtained by lectin and CD31 staining were highly correlated ($r^2$=0.95). (S)-Methyl-2-naphthoylamino-3-(4-nitrophenyl)propionate (SB328437; Calbiochem) dissolved in DMSO was injected into the vitreous humor of wild-type mice using a 33-gauge double-caliber needle (Ito Corporation) immediately after laser injury.

Figure 6:
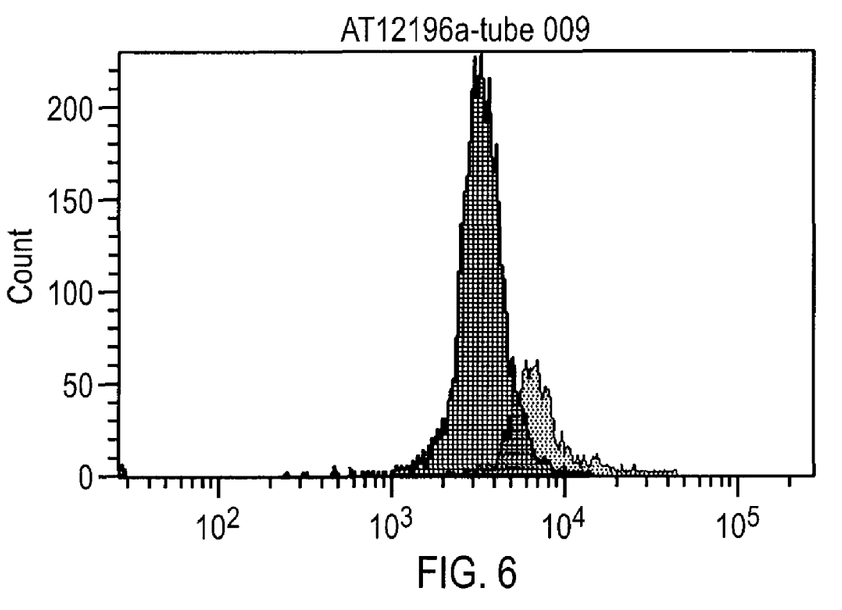
FIG. 6 shows the effect of laser injury on the number of CCR3 receptors in vivo on proliferating and quiescent mouse choroidal endothelial cells.
Figure 7:
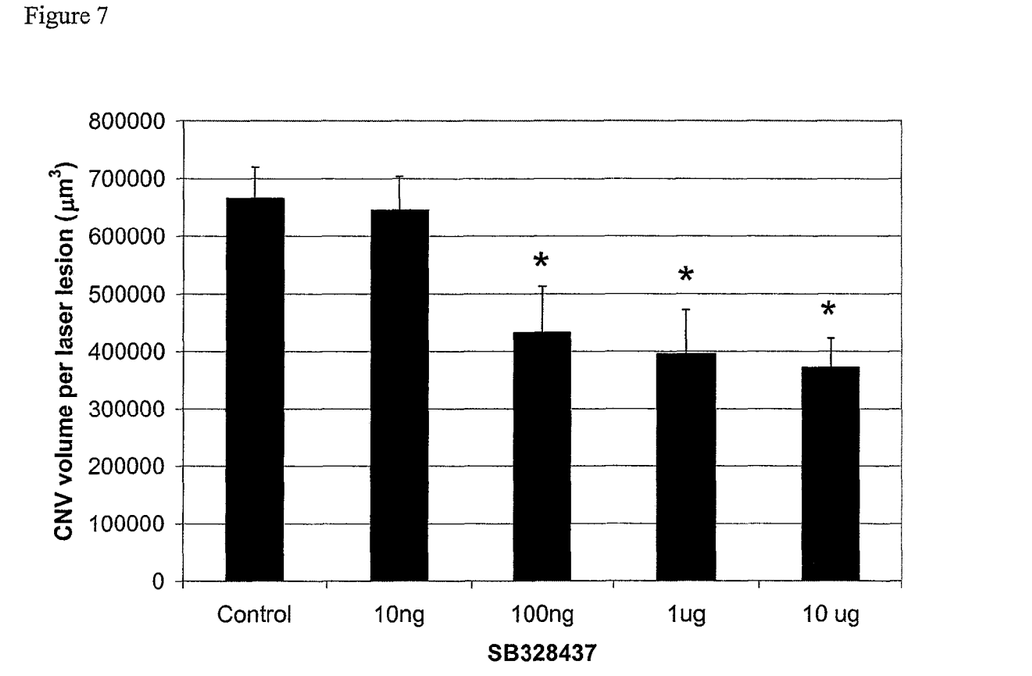
FIG. 7 illustrates the dose-dependent reduction in CNV volume caused by the CCR3 small molecule antagonist SB328437 ((S)-methyl-2-naphthoylamino-3-(4-nitrophenyl) propionate.
Figure 8A:
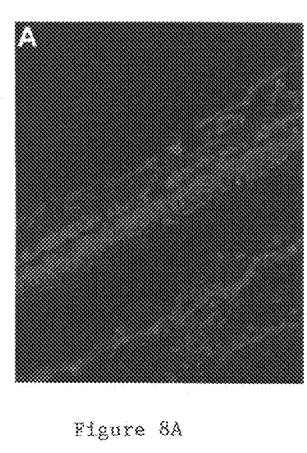
FIGS. 8(A), 8(B) and 8(C) present immunohistochemical analysis of the expression of CCR3 in the retina and choroid of normal patients and patients with age-related macular degeneration.
Figure 8B:
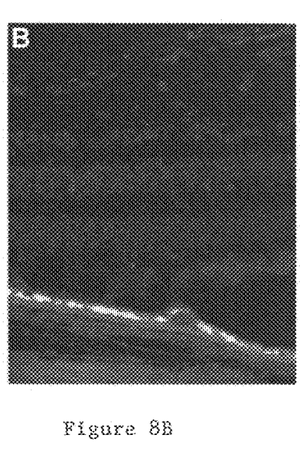
Figure 8C:
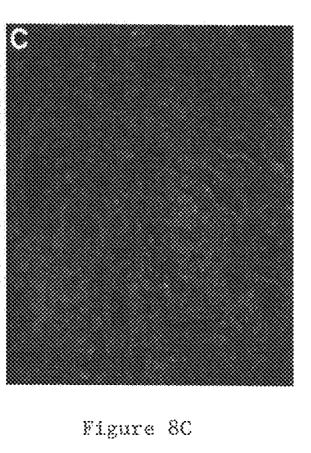

Suspensions of cells isolated from mouse RPE/choroid by incubation with collagenase D (20 U/ml; Roche Diagnostics) treatment were incubated in Fc block (0.5 mg/ml; BD Pharmingen) for 15 min on ice. Rat antibody to mouse CCR3 (1:250; Santa Cruz) coupled with PE-donkey antibody to rat IgG (1:250; Jackson Immunoresearch) were used to quantify cell surface receptor expression on choroidal endothelial cells, defined by $CD31^+VEGFR-2^+$ expression. DNA content for cell cycle was analyzed after incubation with propidium iodide (0.05 mg/ml; Molecular Probes) containing 0.1% Triton X-100 and RNase A (0.1 mg/ml; Roche). Paraffin embedded sections of human eyes or CNV membranes were stained with antibodies against human CCR3 or human vWF and identified with Cy2 or Cy3 secondary antibodies.
Results As illustrated by FIG. 6, following laser injury there is a significantly greater number of CCR3 receptors in vivo on proliferating mouse choroidal endothelial cells (S+G2/M cell cycle phase; light curve) than the number on quiescent cells (G0/G1 phases; dark curve). The results indicate that there is upregulation of CCR3 receptors on the proliferating cells. FIG. 7 shows that the CCR3 small molecule antagonist SB328437 ((S)-methyl-2-naphthoylamino-3-(4-nitrophenyl) propionate) reduces CNV volume in a dose-dependent and statistically significant manner compared to vehicle control (DMSO). In FIG. 8(A), immunohistochemistry shows that CCR3 is expressed in the neural retina of patients without age-related macular degeneration (AMD) but not in the choroid. In FIG. 8(B), CCR3 expression is reduced in the retina and absent in the choroid of patients with AMD who have drusen but not choroidal neovascularization (CNV). FIG. 8(C) shows that CCR3 is highly expressed in the endothelial cells of a CNV membrane excised from a patient with AMD, both on endothelial cells and in the stroma.

Example 3

A F-actin polymerization assay was performed. 10,000 cells from early passage primary hCEC isolates (n=3) were seeded in black-walled 96-well plates and grown to 70-80% confluency in fully supplemented EGM-2MV. Cultures were serum starved overnight in basal media and then stimulated with recombinant human eotaxin-1 (10 ng/mL), eotaxin-2 (100 ng/mL), eotaxin-3 (2 μg/mL) (Peprotech), or vehicle control (PBS). At 0, 10, 30, 60, or 120 second time-points (n=4 per group), cells were fixed in 3.7% paraformaldehyde for 10 minutes, washed, permeabilized in PBS with 0.1% Triton-X, and then stained with rhodamine labeled Phalloidin (1:200, Invitrogen) per manufacturer's recommendations. Plates were analyzed on a fluorescent plate reader (Synergy 4, Biotek) followed by fluorescent microscopy (Nikon E800).

Figure 9:
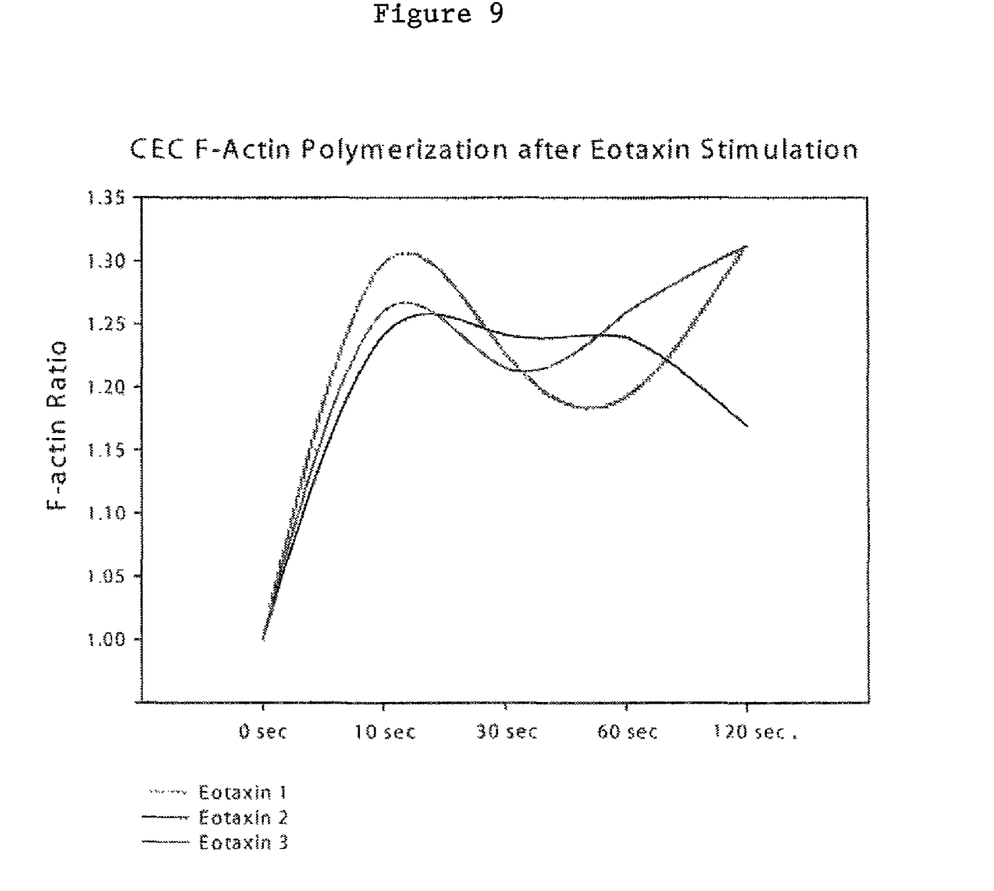
FIG. 9 a graph of the CEC F-actin polymerization after eotaxin stimulation. Polymerization peaked at 10 seconds after stimulation with all eotaxins (eotaxin-1>eotaxin-3>eotaxin-2). Eotaxin-1 and -3 also induced a second delayed burst of F-actin polymerization between 30 and 60 seconds. PBS controls resulted in no significant increase in F-actin polymerization from baseline.
Figure 10A:
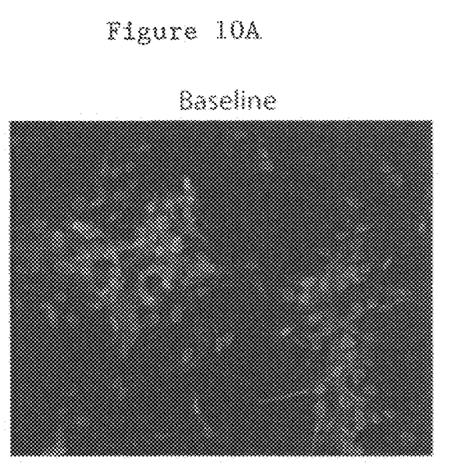
Figure 10B:
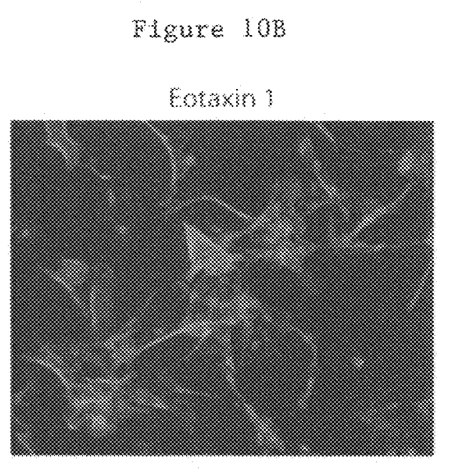
FIG. 10B shows assay results with eotaxin 1.
Figure 10C:
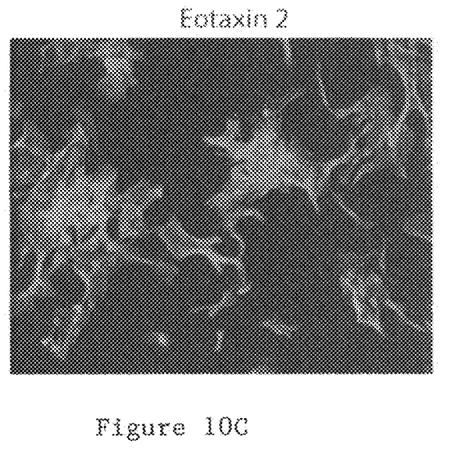
FIG. 10C shows assay results with eotaxin 2.
Figure 10D:
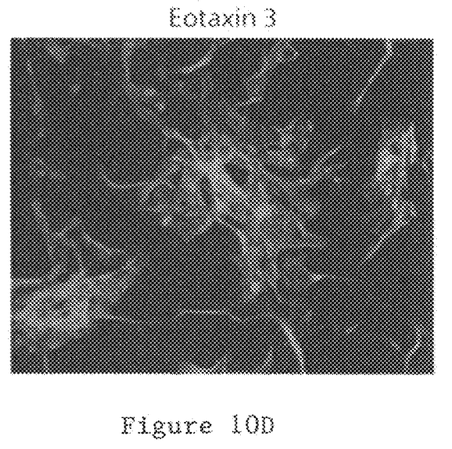

F-actin polymer ratios between baseline and treated cultures were calculated using a fluorescent based plate assay. As seen in FIG. 9, polymerization peaked at 10 seconds after stimulation with all eotaxins (eotaxin-1>eotaxin-3>eotaxin-2). Eotaxin-1 and -3 also induced a second delayed burst of F-actin polymerization between 30 and 60 seconds. PBS controls resulted in no significant increase in F-actin polymerization from baseline.

As shown in FIG. 10, fluorescent microscopic images showed minimal fluorescence in untreated baseline cultures that were approximately 70-80% confluent. After 10 seconds of eotaxin stimulation, hCEC cultures exhibited increased fluorescence and cord characteristic of F-actin polymerization.

Example 4

Figure 11A:
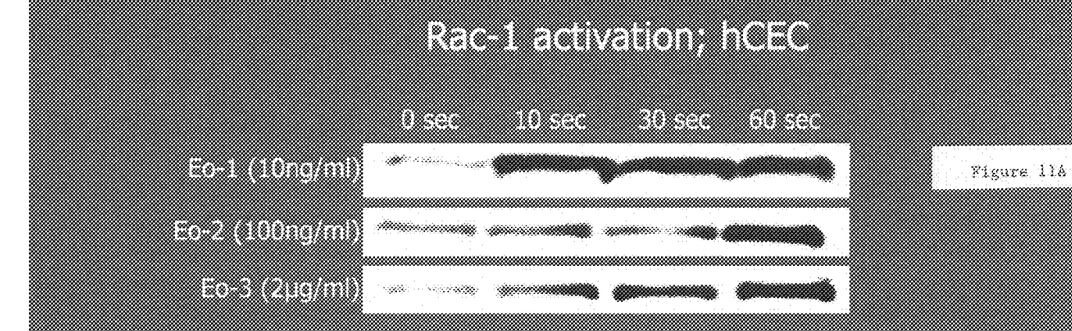
FIG. 11A shows that eotaxins activate Rac-1 GTPase in Human CECs (hCECs). hCECs) were stimulated with Eotaxin-1, 2 and 3 for the indicated times. Cells without Eotaxin stimulation were used as a control (0 sec).
Figure 11B:
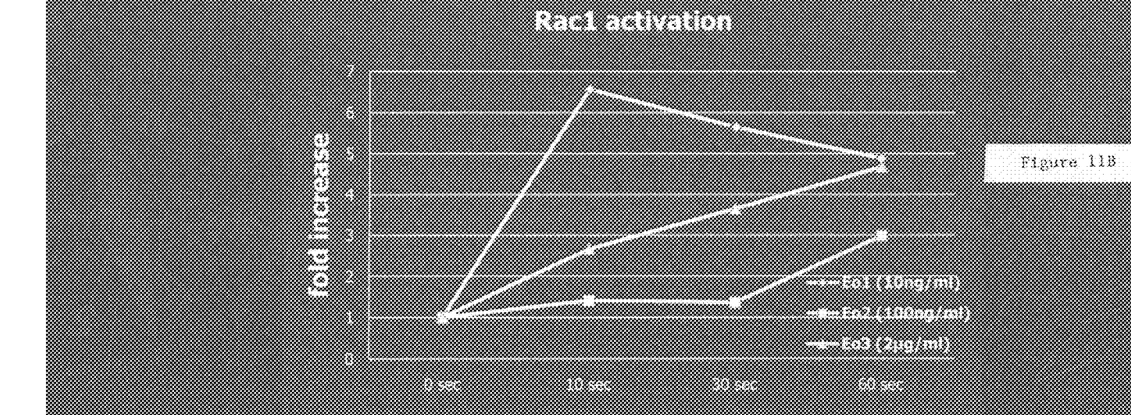
FIG. 11B shows a graph of the levels of increase of active Rac-1, measured after normalizing against the control band density. Eotaxin-1 stimulation showed about 6.5 fold increase of Rac-1 activation at 10 seconds (diamonds). Eotaxin-2 and Eotaxin-3 stimulation showed 3 to 5 fold increase of Rac-1 activation peaking at 60 seconds (squares and triangles respectively).

A Rac-1 activation assay was performed. Human CECs were cultured in EGM-2 MV containing 5% FBS. Prior to starting the assay, cells were serum starved with basal medium (MCDB131) supplemented with 1% FBS overnight. Cells were stimulated for designated times with Eotaxin-1, 2 and 3 (10 ng/ml, 100 ng/ml and 2 μg/ml respectively). Equal amounts of lysates (500 μg) were incubated with GST-Pak1-PBD agarose beads (Upstate) to pull-down active GTP-bound Rac-1 at 4° C. for 1 hour with rotation. The samples were subsequently analyzed for bound Rac-1 by western blot analysis using an anti-Rac-1 antibody (Upstate). Band density was measured using VisionWorksLS software (UVP).

hCECs) were stimulated with Eotaxin-1, 2 and 3 for indicated times. Cells without Eotaxin stimulation were used as a control (0 sec). Equal amount (500 μg) of total cell lysates was used to determine the GTP-bound Rac-1 (active) by pull-down assays. Levels of increase of active Rac-1 were measured after normalizing against the control band density. As shown in FIG. 11B, eotaxins activated Rac-1 GTPase in Human CECs (hCECs). Eotaxin-1 stimulation showed about 6.5 fold increase of Rac-1 activation at 10 seconds. Eotaxin-2 and Eotaxin-3 stimulation showed 3 to 5 fold increase of Rac-1 activation peaking at 60 seconds.

All references cited in this disclosure are incorporated by reference to the same extent as if each reference had been incorporated by reference in its entirety individually.

While the invention has been described in detail and with reference to specific embodiments thereof, it will be apparent to one skilled in the art that various variations and modifications can be made therein without departing from the sprit and scope thereof. All such variations and modifications are intended to be included within the scope of this disclosure and the present invention and protected by the following claims.

I claim:

1. A method of diagnosing or monitoring choroidal neovascularization or wet macular degeneration, comprising administering a labeled CCR3-specific binding molecule to a patient and detecting the presence or absence of the labeled CCR3-specific binding molecule in the choroid of the patient, wherein the presence of the labeled CCR3-specific binding molecule being indicative of choroidal neovascularization or wet macular degeneration in said patient.

* * * * *